(12) United States Patent
Gassa et al.

(10) Patent No.: US 10,329,311 B1
(45) Date of Patent: Jun. 25, 2019

(54) PROCESS FOR THE PREPARATION OF CRISABOROLE

(71) Applicant: OLON S.p.A., Rodano (IT)

(72) Inventors: Federico Gassa, Lodigiano (IT); Lazzaro Feliciani, Lodigiano (IT); Alberto Mazza, Lodigiano (IT); Marco Quaroni, Lodigiano (IT); Mara Sada, Lodigiano (IT); Giorgio Bertolini, Lodigiano (IT)

(73) Assignee: OLON S.P.A., Rodano (IT)

( * ) Notice: Subject to any disclaimer, the term of this patent is extended or adjusted under 35 U.S.C. 154(b) by 0 days.

(21) Appl. No.: 15/927,264

(22) Filed: Mar. 21, 2018

(30) Foreign Application Priority Data

Dec. 21, 2017 (IT) .................. 102017000148330

(51) Int. Cl.
| | | |
|---|---|---|
| *C07F 5/02* | (2006.01) | |
| *C07C 39/205* | (2006.01) | |
| *B01J 27/053* | (2006.01) | |
| *B01J 23/44* | (2006.01) | |
| *B01J 23/42* | (2006.01) | |
| *C07C 39/15* | (2006.01) | |
| *C07C 37/02* | (2006.01) | |
| *B01J 27/232* | (2006.01) | |

(52) U.S. Cl.
CPC .............. *C07F 5/027* (2013.01); *B01J 23/42* (2013.01); *B01J 23/44* (2013.01); *B01J 27/053* (2013.01); *B01J 27/232* (2013.01); *C07C 37/02* (2013.01); *C07C 39/15* (2013.01); *C07C 39/205* (2013.01); *C07F 5/025* (2013.01)

(58) Field of Classification Search
None
See application file for complete search history.

(56) References Cited

U.S. PATENT DOCUMENTS

2015/0291629 A1 10/2015 Akama

OTHER PUBLICATIONS

Akama et al., "Discovery and structure-activity study of a novel benzoxaborole anti-inflammatory agent (AN2728) for the potential topical treatment of psoriasis and atopic dermatitis," Bioorganic & Medicinal Chemistry Letters, Apr. 15, 2009, pp. 2129-2132, vol. 19, No. 8.
Italian Search Report and Written Opinion issued in IT 201700148330 dated May 29, 2018.

*Primary Examiner* — Rosalynd A Keys
(74) *Attorney, Agent, or Firm* — Arent Fox LLP

(57) ABSTRACT

The present invention relates to a process for the preparation of crisaborole of formula (I):

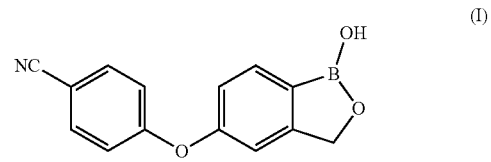

by preparing intermediates of formulas (II) and (III):

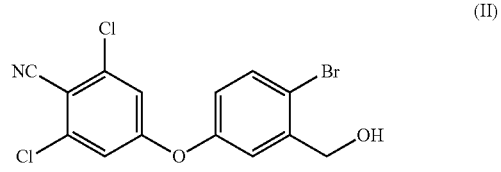

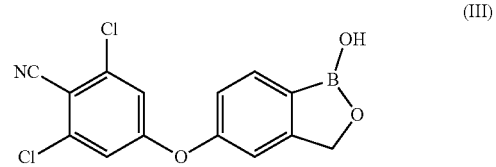

14 Claims, No Drawings

PROCESS FOR THE PREPARATION OF CRISABOROLE

CROSS-REFERENCE TO RELATED APPLICATON

This application claims priority to Italian Patent Application No. 102017000148330, filed Dec. 21, 2017. The disclosure of the priority application is incorporated in its entirety herein by reference.

The present invention relates to a process for the preparation of Crisaborole, a non-steroidal medicament used for the treatment of atopic dermatitis. The invention also relates to novel synthesis intermediates.

TECHNICAL CONTEXT

Crisaborole is the international non-proprietary name of the compound 5-(4-cyanophenoxy)-1,3-dihydro-1-hydroxy-2,1-benzoxaborole having formula (I):

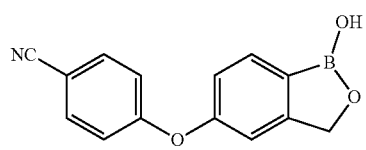

(I)

Crisaborole is the active ingredient of Eucrisa, a topical non-steroidal medicament approved by the FDA in the USA for the treatment of atopic dermatitis in patients from two years old. The molecule is currently undergoing clinical trials (phase II) for the treatment of (inter alia) psoriasis.

Crisaborole and its synthesis route were described and claimed for the first time in patent application WO2006/089067 by Anacor Pharmaceutical Inc. No alternative synthesis routes to the one described in the originator's patent and publications exist to date.

The synthesis route used in WO2006/089067 (scheme) involves numerous steps, and the total yield is not very high, which makes the process expensive.

Scheme

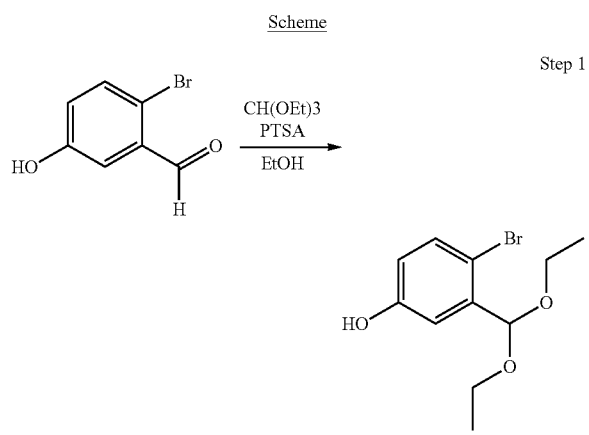

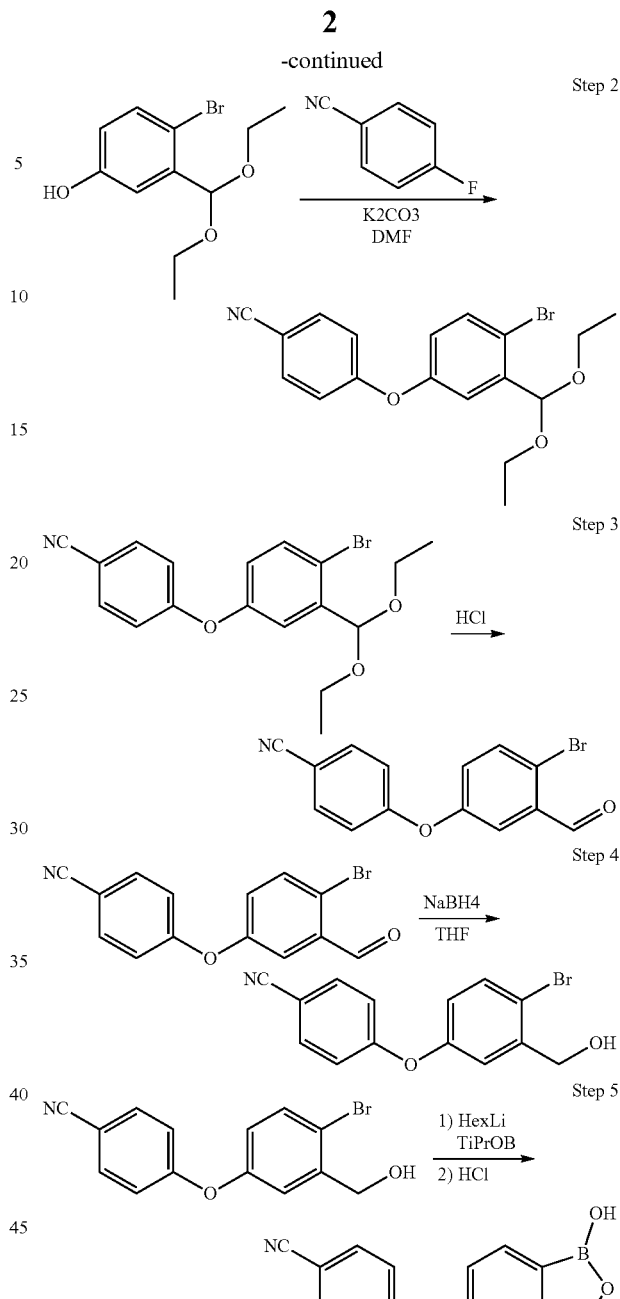

It has surprisingly been found that by using a dichloroaryl intermediate of formula (V), as defined below, activated in the ortho position to the nitrile group by two electron-attracting groups, in particular two halogens, the reactions indicated in the 2-bromo-hydroxybenzaldehyde protection step (step 1) and the nucleophilic substitution reaction between the protected aldehyde and the fluorinated intermediate and subsequent reduction of the resulting product (step 2) can be replaced by a one-pot reaction, thus eliminating several steps.

The process according to the invention produces Crisaborole with a high degree of purity and excellent yields, and can be effected on an industrial scale.

DESCRIPTION OF THE INVENTION

The object of the present invention is a process for the preparation of Crisaborole of formula (I):

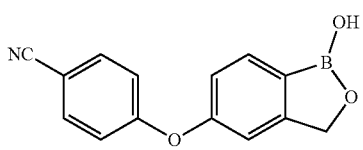

(I)

wherein said process comprises the following steps:
a) converting compound of formula (II):

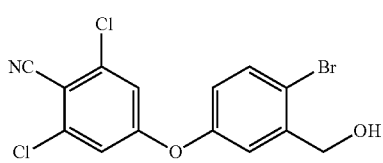

(II)

to compound of formula (III):

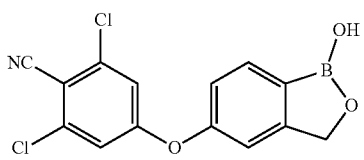

(III)

in the presence of a tri ($C_1$-$C_4$) alkyl borate and a ($C_4$-$C_6$) alkyl lithium or aryl lithium, and subsequent acidification of the reaction medium; and
b) converting the resulting compound of formula (III) to Crisaborole of formula (I) by catalytic hydrogenation.

The term ($C_4$-$C_6$) alkyl, as used herein, means a straight or branched alkyl chain having 4 to 6 carbon atoms such as n-hexyl, n-pentyl, n-butyl, isobutyl, isopentyl or tert-butyl.

The term ($C_1$-$C_4$) alkyl, as used herein, means a straight or branched alkyl chain having 1 to 4 carbon atoms such as methyl, ethyl, n-propyl, isopropyl, n-butyl or isobutyl.

The ($C_4$-$C_6$) alkyl lithium used in step a) of the process described above is preferably selected from butyl lithium and hexyl lithium.

The tri ($C_1$-$C_4$) alkyl borate used in step a) is preferably selected from trimethyl borate and triisopropyl borate.

Step a) is effected in a polar aprotic solvent such as cyclic or linear ethers or mixtures thereof, preferably tetrahydrofuran or methyl tetrahydrofuran, at a temperature ranging between −30° and −80° C.

The reaction medium is preferably acidified with acids such as hydrochloric acid, sulphuric acid, acetic acid and formic acid, in particular hydrochloric acid or acetic acid.

The catalytic hydrogenation of step b) is effected with palladium or platinum catalysts supported on carbon, barium sulphate or barium carbonate, such as 5% palladium on carbon, in a solvent such as ether, alcohol or water or in mixtures, at a temperature ranging between 0° and 50° C.

A further object of the invention is the process for the preparation of Crisaborole of formula (I) as described above, wherein compound of formula (II) is obtained by the following steps:

i) reacting compound of formula (IV):

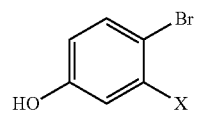

(IV)

wherein X is —COH or —CH$_2$OH, with compound of formula (V):

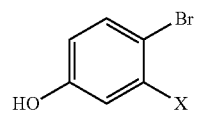

(V)

in the presence of an inorganic base, to give compound of formula (II) when X is —CH$_2$OH or compound of formula (VI) when X is —COH:

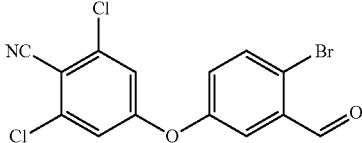

(VI)

and
ii) reducing compound of formula (VI) to give compound of formula (II).

The nucleophilic substitution reaction of step i) is effected in polar aprotic solvents such as toluene, dimethyl formamide, dimethylacetamide and methyl isobutyl ketone or mixtures thereof, preferably dimethyl formamide or dimethylacetamide, in the presence of inorganic bases such as alkali metal or alkaline-earth metal carbonates, in particular potassium carbonate.

The reaction is effected at a temperature ranging between 0° and 80° C.

The reduction reaction of step ii) is effected with reducing compounds such as KBH$_4$, NaBH4 and LiBH$_4$ (potassium borohydride, sodium borohydride and lithium borohydride), preferably NaBH4, in polar aprotic solvents such as THF, MeTHF, DMF and DMA (tetrahydrofuran, methyltetrahydrofuran, dimethylformamide, dimethylacetamide) or mixtures thereof, preferably tetrahydrofuran or methyltetrahydrofuran, at a temperature ranging between 0° and 50° C.

Another object of the invention is the process described above wherein compound of formula (IV), wherein X is —COH, is reacted with compound of formula (V), and steps i) and ii) are effected without isolating compound of formula (VI) (one-pot reaction).

Nucleophilic substitution reaction i) and reduction reaction ii), effected without isolating intermediate (VI), can be carried out by operating in solvents such as DMF, DMA and toluene or mixtures thereof, where necessary adding a phase-transfer catalyst such as tetrabutylammonium bromide, benzyl triethylammonium chloride, hexadecyl trimethylammonium bromide, tetrabutylammonium hydrogen sulphate and tetramethylammonium chloride (preferably tetrabutylammonium bromide).

Both reactions are effected at a temperature ranging between 0° and 120° C.

Compound of formula (IV) wherein X is —CH₂OH can be obtained by reducing compound of formula (IV) wherein X is —COH. Compound of formula (IV) wherein X is —COH is a commercial product.

The reduction of compound of formula (IV) wherein X is —COH can be effected in the presence of a reducing reagent such as potassium borohydride, sodium borohydride or lithium borohydride, preferably sodium borohydride, in polar aprotic solvents selected from tetrahydrofuran, dioxane, methyltetrahydrofuran, dimethyl formamide, dimethyl acetamide and toluene or mixtures thereof, preferably tetrahydrofuran or methyltetrahydrofuran.

The reaction is effected at a temperature ranging between 0 and 30° C.

Compound of formula V is a commercial product or obtainable by known processes from commercial products.

A further object of the invention is the reaction intermediates of formulae (II) and (III).

The process for the preparation of Crisaborole disclosed in WO2006/089067, and in *Bioorg. Med. Chem. Lett:* 19 (2009) 2129-2132 by the same authors, involves five chemical steps and a total yield of 32% (mean values of the methods described), and also involves lengthy reactions, with hot treatments (100° C.). The processing of the intermediates involves distillations of large amounts of solvent, which are expensive and not very safe. No less than four chemical steps (aldehyde protection and alkylation, followed by deprotection and reduction) are required to obtain the key intermediate, and although they produce fairly good yields, they are lengthy and expensive.

In a preferred embodiment thereof, the process of the invention, starting with 2-bromo-5-hydroxybenzaldehyde or the corresponding alcohol (2-bromo-5-hydroxy phenylmethanol), enables the key intermediate (4-(4-bromo-3-(hydroxymethyl)phenoxy)-2,6-dichlorobenzonitrile) to be prepared without isolating intermediates, operating at room temperature. The product is isolated by simple filtration after adding water as antisolvent to the reaction mixture. This is possible due to the addition of two chlorine atoms to the 4-fluoro benzonitrile, which activate the aromatic nucleophilic substitution reaction. The two chlorine atoms are then removed to obtain Crisaborole by reduction. Despite the addition of this step, the process of the invention only consists of three steps, as against five. The total yield is higher (74% vs. 32%), the operating conditions are milder, and the processes are simpler and safer.

EXAMPLES

Example 1

Synthesis of 4-bromo-3-(hydroxymethyl)phenol (Compound of Formula (IV) Wherein X is —CH₂OH)

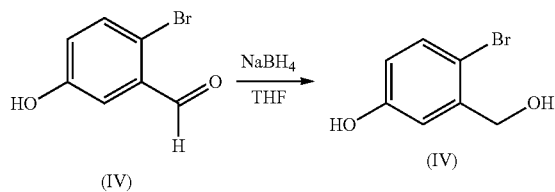

2-Bromo-5-hydroxy benzaldehyde (compound of formula IV wherein X is —COH) (20.1 g, 100 mmol) was dissolved in THF (80 mL), and the solution was cooled to 0-5° C. A solution of NaBH4 (1.9 g, 50 mmol) in water (10 mL, stabilised with NaOH) was added in 30 min. The solution was stirred for a further 30 min. Acetone (25 mL) was added dropwise to the solution in 30 min. Water (50 mL) was then added, and THF was distilled off. The residual oil was extracted with AcOEt (200 mL). The organic phase was washed with saline solution (50 mL), then AcOEt was distilled off. The resulting solid was treated at 50° C. with 50 mL of toluene, and the suspension cooled to 20° C. The solid was filtered and dried at 65° C. to obtain the title compound as a white solid (18.6 g, 91%).

¹H-NMR; 300 MHz, DMSO-d₆. δ 9.64 (brs, 1H), 7.27 (d, 1H), 7.01 (d, 1H), 6.60 (dd, 1H), 5.37 (brs, 1H), 4.41 (s, 2H)

¹³C-NMR; 300 MHz, DMSO-d₆. δ 157.5, 142.4, 132.9, 115.9, 115.6, 109.4, 63.0.

Example 2

Synthesis of 4-(4-bromo-3-(hydroxymethyl)phenoxy)-2,6-dichlorobenzonitrile of Formula (II)

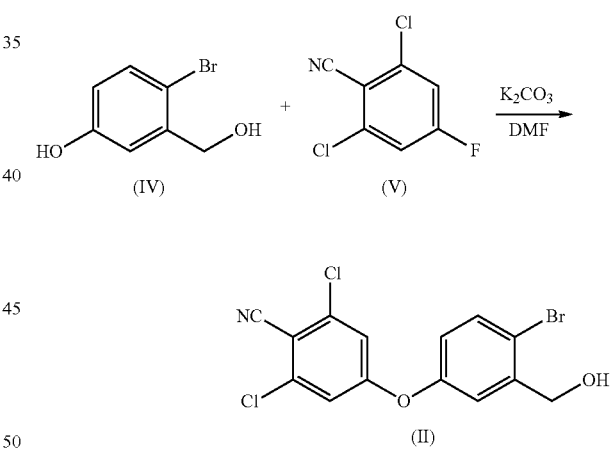

4-Bromo-3-(hydroxymethyl)phenol (5.0 g, 25 mmols) (compound of formula (IV) wherein X is —CH₂OH) was dissolved in DMF (30 mL). 2.6 Dichloro-4 fluorobenzonitrile (4.9 g, 26 mmol) (compound of formula (V)) and K₂CO₃ (3.9 g, 28 mmols) were added, and the suspension was stirred for 5 hours. Water (100 mL) was added, and compound of formula (II) was collected as a white solid by filtration (7.3 g, 19.6 mmols, 80%).

¹H-NMR; 300 MHz, DMSO-d₆. δ 7.65 (d, 1H), 7.30 (d, 1H), 7.06 (dd, 1H), 5.55 (t, 1H), 4.49, (d, 2H).

¹³C-NMR; 300 MHz, DMSO-d₆. δ 161.8, 153.6, 144.4, 139.1, 134.4, 120.9, 102.1, 118.0, 117.4, 114.0, 107.5, 62.8.

Example 3

Synthesis of 2,6-dichloro-4-((1-hydroxy-1,3-dihydrobenzo[c][1,2]oxaborol-5-yl)oxy)benzonitrile of Formula (III)

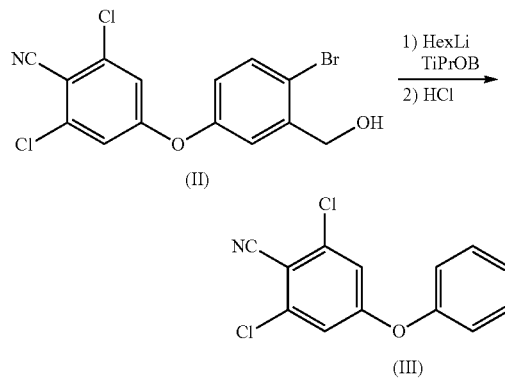

4-(4-Bromo-3-(hydroxymethyl)phenoxy)-2,6-dichlorobenzonitrile of formula (II) (50.0 g, 164 mmols), 3,4-dihydropyran (34.9 g, 415 mmols) and pyridinium p-toluenesulphonate (2.0 g, 8 mmols) were stirred in THF for 24 hours. TiPrOB (49.2, 262 mmols) was added, and the solution was cooled to −78° C. A hexyllithium 2.3 molar solution in hexane was added dropwise in 40 min., and the final mixture was stirred at said temperature for 90 min. The solution was heated to room temperature and kept under stirring at said temperature for a total of 2 hours. THF was then distilled off. 100 mL of 6N HCl was added slowly, and the suspension was stirred for 16 hours. EtOH (400 mL) was added, and compound of formula (III) was obtained by filtration (36.0 g, 112 mmols, 84%).

$^1$H-NMR; 300 MHz, DMSO-$d_6$. δ 9.25 (s, 1H), 7.82 (d, 1H), 7.33 (s, 2H), 7.23 (d, 1H), 7.15 (dd, 1H), 4.98 (s, 2H)

$^{13}$C-NMR; 300 MHz, DMSO-$d_6$. δ161.8, 157.2, 156.4, 139.1, 133.2, 119.6, 118.4, 114.1, 113.7, 107.5, 70.1

Example 4

Synthesis of Crisaborole of Formula (I)

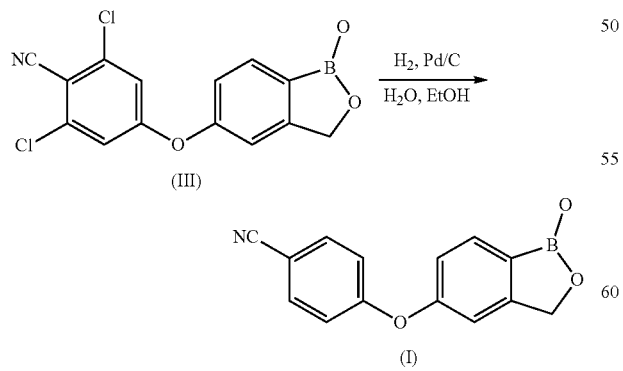

2,6-Dichloro-4-((1-hydroxy-1,3-dihydrobenzo[c][1,2]oxaborol-5-yl)oxy)-benzonitrile (10.0 g, 31 mmols) and KOH (5.0 g, 84 mmols) were suspended in a mixture of ethanol (100 mL) and water (100 mL). 5% Pd on carbon (1.0 g) was then added, and the mixture was placed under hydrogen atmosphere at 1-5 ATM. The reaction was completed after 1 h, and the catalyst was filtered off. 37% Hydrochloric acid was added to the filtered solution to obtain a pH of less than 2. The solution was concentrated under vacuum at 50 mL, and a white solid precipitated. The suspension was cooled to room temperature and stirred for 1 hour. Crisaborole was then isolated by filtration (7.0 g, 28 mmol, 90%).

Example 5

Synthesis of 4-(4-bromo-3-(hydroxymethyl)phenoxy)-2,6-dichlorobenzonitrile (One-Pot Reaction in DMA) of Formula (II)

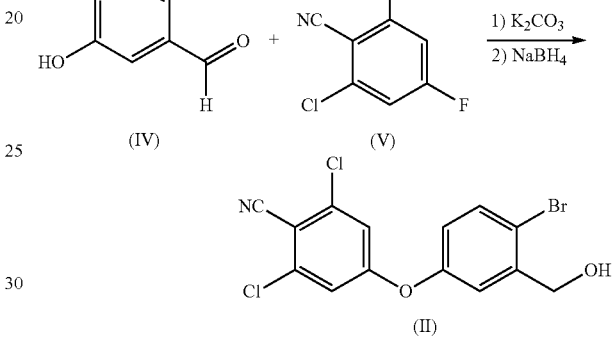

2-Bromo-5-hydroxybenzaldehyde (30.0 g, 149 mmols) and 2,6-dichloro-4-fluorobenzonitrile (30.0 g, 158 mmols) were dissolved in DMA (130 mL), and $K_2CO_3$ (27.0 g, 195 mmols) was added to the solution. The reaction was maintained at 20-30° C. for 3-6 hours, after which a solution of NaBH4 (2.0 g, 53 mmols) in water (20 mL), stabilised with 5% NaOH) was added in 20 min. The solution was kept under stirring for a further 30 min., then water (500 mL) was added. The solution was kept under stirring for 1 hour, and the title product was isolated as a white solid by filtration (54.6 g, 146 mmols, 98%).

Example 6

Synthesis of 4-(4-bromo-3-(formylphenoxy)-2,6-dichlorobenzonitrile of Formula (VI)

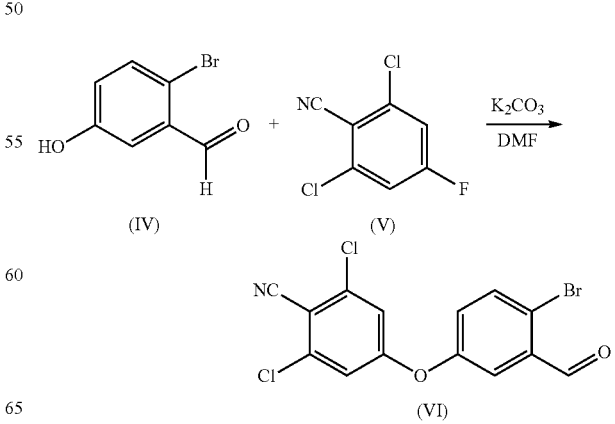

2-Bromo-5-hydroxy benzaldehyde (30.0 g, 149 mmols) was dissolved in DMF (120 mL), 2,6-dichloro-4-fluorobenzonitrile (30.0 g, 158 mmols) and K$_2$CO$_3$ (27.0 g, 195 mmols) were added to the solution, and the suspension was stirred for 1-4 h, maintaining the temperature under 30° C. Water (300) mL) was added, and a white solid was collected by filtration and washing with water (100 mL). (54.2 g, 146 mmol, 97%).

$^1$H-NMR; 300 MHz, CDCl$_3$. δ 10.33 (s, 1H), 7.76 (d, 1H), 7.60 (d, 1H), 7.22 (dd, 1H), 6.98 (s, 2H)

$^{13}$C-NMR; 300 MHz, CDCl$_3$. δ 190.5, 160.6, 153.7, 139.9, 136.1, 135.2, 127.3, 123.2, 117.3, 113.2, 109.1.

Example 7

Synthesis of 4-(4-bromo-3-(hydroxymethyl)phenoxy)-2,6-dichlorobenzonitrile of Formula (II)

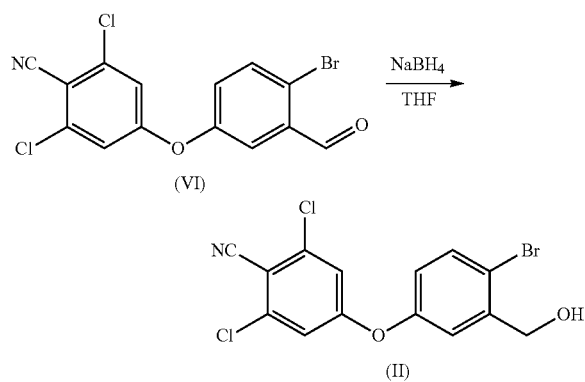

4-(4-Bromo-3-formylphenoxy)-2,6-dichlorobenzonitrile (77.8 g, 210 mmols) was dissolved in THF (365 mL), and the solution was cooled to 0-5° C. A solution of NaBH4 (2.7 g, 71 mmols) in water (25 mL, stabilised by NaOH) was added in 1 hour. The solution was kept under stirring for a further 30 min. Acetone (25 mL) was added dropwise in 30 min., then water (150 mL) was added. THF was distilled off, and a solid precipitate was obtained. The suspension was cooled to room temperature, and the product was isolated as a white solid by filtration (77.6 g, 208 mmols, 98%). The crude product was suspended in toluene (320 mL) and placed under reflux for 30 minutes. The solution was slowly cooled to room temperature, and the pure white solid was recovered by filtration (75.3 g, 95%).

Example 8

Synthesis of 4-(4-bromo-3-(hydroxymethyl)phenoxy)-2,6-dichlorobenzonitrile of Formula (II) (Phase-Transfer Conditions)

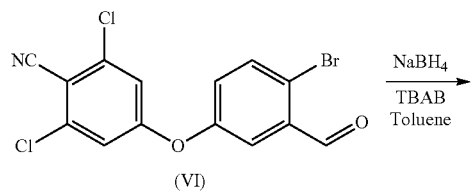

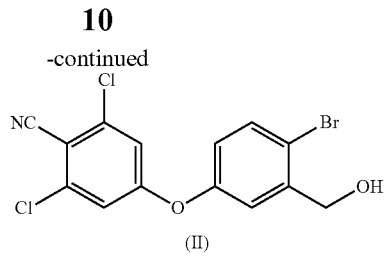

4-(4-Bromo-3-formylphenoxy)-2,6-dichlorobenzonitrile (15.0 g, 40 mmols) and TBAB (0.15 g, 0.5 mmols) were suspended in toluene (140 mL), and the solution was heated to 45-50° C. A solution of NaBH4 (0.6 g, 16 mmol) in water (6 mL, stabilised with NaOH) was added in 10 min. The solution was kept under stirring for a further 60 min. Acetic acid (3.6 g) was added dropwise in 30 min., and the mixture was then kept under stirring for 30 min. The suspension was heated to 80° C., and the aqueous phase was separated. 70 mL of toluene was distilled off, and the solution was cooled to room temperature. The product was isolated as a white solid by filtration (13.0 g, 35 mmols, 88%).

Example 9

Synthesis of 4-(4-bromo-3-(hydroxymethyl)phenoxy)-2,6-dichlorobenzonitrile of Formula (II) (Reaction in Phase-Transfer Conditions)

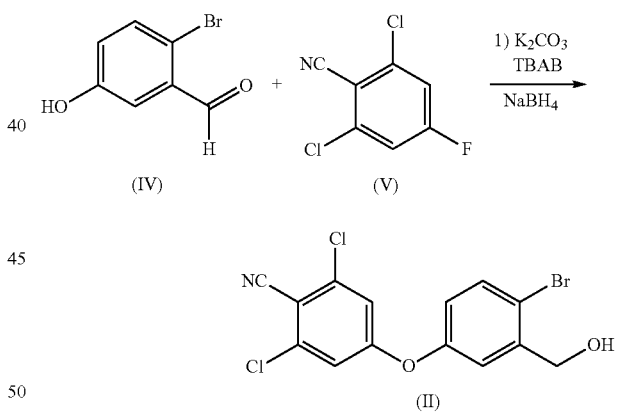

2-Bromo-5-hydroxy-benzaldehyde (10.0 g, 50 mmols), 2,6-dichloro-4-fluoro benzonitrile (9.9 g, 52 mmols), K$_2$CO$_3$ (8.9 g, 64 mmols) and TBAB (1 g, 0.3 mmols) were suspended in toluene (100 mL), and the solution was heated to 70° C. for 24 hours. The solution was cooled to room temperature and washed twice with water (50 ml). A solution of NaBH4 (0.65 g, 170 mmols) in water (15 mL) was added dropwise, and the solution was kept under stirring for a further 30 min. The solution was washed twice with water (50 mL) and concentrated to 40 mL. The solution was then cooled to room temperature, and the product was isolated as a white solid by filtration (16.6 g, 44 mmols, 88%).

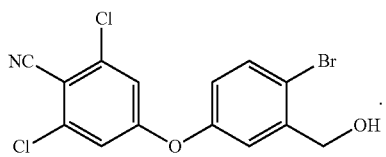

14. Compound of formula (III):
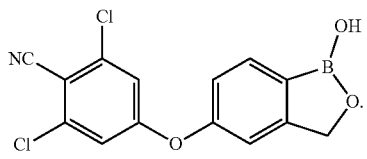

The invention claimed is:

1. A process for the preparation of Crisaborole of formula (I):

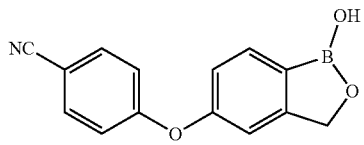

wherein said process comprises the following steps:
a) converting compound of formula (II):

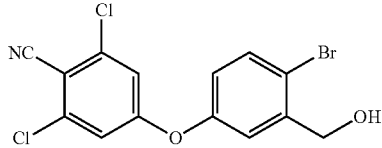

into compound of formula (III):

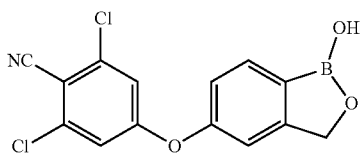

in the presence of a tri ($C_1$-$C_4$) alkyl borate and a ($C_4$-$C_6$) alkyl lithium or aryl lithium and subsequent acidification of the reaction medium; and
b) converting the resulting compound of formula (III) into Crisaborole of formula (I) by catalytic hydrogenation.

2. The process according to claim 1, wherein the ($C_4$-$C_6$) alkyl lithium used in process step a) is selected from butyl lithium and hexyl lithium.

3. The process according to claim 1, wherein the tri ($C_1$-$C_4$) alkyl borate used in step a) is selected from trimethyl borate and triisopropyl borate.

4. The process according to claim 1, wherein step a) is carried out in a solvent selected from cyclic or linear ethers or mixtures thereof.

5. The process according to claim 1, wherein the catalytic hydrogenation of step b) is carried out with palladium or platinum catalysts supported on carbon, barium sulphate or barium carbonate.

6. The process according to claim 1, wherein compound of formula (II) is obtained by the following steps:
i) reacting compound of formula (IV):

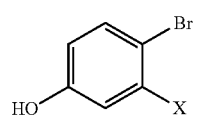

wherein X is —COH or —CH$_2$OH, with compound of formula (V):

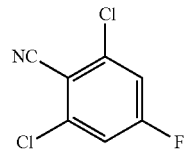

in the presence of an inorganic base, to give compound of formula (II) when X is —CH$_2$OH, or compound of formula (VI) when X is —COH:

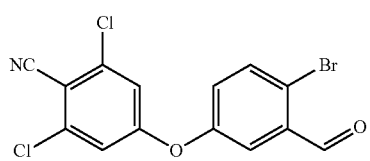

and
ii) reducing compound of formula (VI) to give compound of formula (II).

7. The process according to claim 6, wherein the reaction of step i) is carried out in an aprotic polar solvent selected from toluene, dimethylformamide, dimethylacetamide, methylisobutylketone or mixtures thereof.

8. The process according to claim 6, wherein the inorganic base is an alkali metal or alkaline earth metal carbonate.

9. The process according to claim 6, wherein the reduction reaction of step ii) is carried out with reducing compounds selected from potassium borohydride, sodium borohydride and lithium borohydride.

10. The process according to claim 9, wherein the reduction is carried out in aprotic polar solvents or mixtures thereof.

11. The process according to claim 6, wherein compound of formula (IV) wherein X is —COH is reacted with compound of formula (V), and steps i) and ii) are carried out without isolating compound of formula (VI).

12. The process according to claim 11, wherein reactions i) and ii) are carried out in an aprotic polar solvent selected from DMF, DMA and toluene or mixtures thereof, optionally in the presence of a phase transfer catalyst selected from tetrabutylammonium bromide, benzyl triethylammonium chloride, hexadecyl trimethylammonium bromide, tetrabutylammonium hydrogen sulphate and tetramethylammonium chloride.

13. Compound of formula (II):